(12) United States Patent
Kim et al.

(10) Patent No.: US 8,986,206 B2
(45) Date of Patent: Mar. 24, 2015

(54) HEALTH CARE APPARATUS AND METHOD

(75) Inventors: Youn-ho Kim, Hwaseong-si (KR);
Kun-soo Shin, Seongnam-si (KR);
Wan-taek Han, Hwaseong-si (KR);
Hyung-sok Yeo, Yongin-si (KR);
Hyun-tai Hwang, Yongin-si (KR);
Jong-pal Kim, Seoul (KR)

(73) Assignee: Samsung Electronics Co., Ltd.,
Suwon-si (KR)

( * ) Notice: Subject to any disclaimer, the term of this patent is extended or adjusted under 35 U.S.C. 154(b) by 1661 days.

(21) Appl. No.: 11/397,716

(22) Filed: Apr. 5, 2006

(65) Prior Publication Data
US 2007/0016098 A1 Jan. 18, 2007

(30) Foreign Application Priority Data

Jul. 16, 2005 (KR) .......................... 10-2005-0064547

(51) Int. Cl.
*A61B 5/00* (2006.01)
*A61B 5/06* (2006.01)
*G06Q 10/00* (2012.01)
*G06Q 50/00* (2012.01)
(Continued)

(52) U.S. Cl.
CPC ........... *A61B 5/0404* (2013.01); *A61B 5/02055* (2013.01); *A61B 5/1118* (2013.01); *A61B 5/1123* (2013.01); *A61B 5/4866* (2013.01); *A61B 5/4884* (2013.01); *G06F 19/3431* (2013.01); *A61B 5/0002* (2013.01); *A61B 5/01* (2013.01); *A61B 5/021* (2013.01); *A61B 5/02416* (2013.01); *A61B 5/0456* (2013.01); *A61B 5/145* (2013.01); *A61B 2560/0462* (2013.01); *A61B 2560/0468* (2013.01); *A61B 2562/0219* (2013.01)

USPC ........... 600/301; 600/544; 600/545; 600/546; 705/2; 705/3

(58) Field of Classification Search
USPC .................. 600/300, 301; 128/903–905, 920
See application file for complete search history.

(56) References Cited

U.S. PATENT DOCUMENTS

| 3,943,918 A | 3/1976 | Lewis |
| 4,110,918 A * | 9/1978 | James et al. .................. 434/262 |

(Continued)

FOREIGN PATENT DOCUMENTS

| JP | 5-076501 A | 3/1993 |
| JP | 6-181891 A | 7/1994 |

(Continued)

*Primary Examiner* — William Thomson
*Assistant Examiner* — Shirley Jian
(74) *Attorney, Agent, or Firm* — Sughrue Mion, PLLC

(57) ABSTRACT

A health care apparatus and method are provided. The apparatus includes: a motion sensing unit; a bio-electric potential sensing unit sensing an electric potential signal of the health examinee corresponding to the sensed result; and an analysis unit analyzing the sensed result. By recognizing a current motion of the examinee and sensing an electric potential signal corresponding to the recognized current motion from the examinee, a more reliable health index of the examinee can be calculated. Even when information on the current motion of the health examinee is not given, the current motion can be recognized by the apparatus and method. Furthermore, since the health examinee is notified of the calculated health index in real time, the health examinee can be informed immediately if the physical condition is in an emergency state. As a result, the examinee can respond quickly to the emergency situation.

25 Claims, 7 Drawing Sheets

(51) Int. Cl.
  *A61B 5/0404* (2006.01)
  *A61B 5/0205* (2006.01)
  *A61B 5/11* (2006.01)
  *G06F 19/00* (2011.01)
  *A61B 5/01* (2006.01)
  *A61B 5/021* (2006.01)
  *A61B 5/024* (2006.01)
  *A61B 5/0456* (2006.01)
  *A61B 5/145* (2006.01)

(56) References Cited

U.S. PATENT DOCUMENTS

| | | | | |
|---|---|---|---|---|
| 5,394,882 A * | 3/1995 | Mawhinney | | 600/534 |
| 5,511,553 A | 4/1996 | Segalowitz | | |
| 5,792,195 A * | 8/1998 | Carlson et al. | | 607/17 |
| 5,862,803 A | 1/1999 | Besson et al. | | |
| 5,964,701 A * | 10/1999 | Asada et al. | | 600/300 |
| 6,026,321 A | 2/2000 | Miyata et al. | | |
| 6,026,324 A * | 2/2000 | Carlson | | 607/27 |
| 6,047,203 A * | 4/2000 | Sackner et al. | | 600/388 |
| 6,366,811 B1 * | 4/2002 | Carlson | | 607/27 |
| 6,441,747 B1 * | 8/2002 | Khair et al. | | 340/870.16 |
| 6,551,252 B2 * | 4/2003 | Sackner et al. | | 600/536 |
| 6,571,193 B1 * | 5/2003 | Unuma et al. | | 702/141 |
| 6,595,929 B2 * | 7/2003 | Stivoric et al. | | 600/549 |
| 6,821,229 B2 * | 11/2004 | Sato et al. | | 482/8 |
| 7,130,681 B2 * | 10/2006 | Gebhardt et al. | | 607/6 |
| 7,299,159 B2 * | 11/2007 | Nanikashvili | | 702/188 |
| 7,604,603 B2 * | 10/2009 | Sackner et al. | | 600/500 |
| 2001/0047127 A1 * | 11/2001 | New et al. | | 600/300 |
| 2002/0180605 A1 | 12/2002 | Ozguz et al. | | |
| 2003/0083559 A1 | 5/2003 | Thompson | | |
| 2003/0171661 A1 * | 9/2003 | Tong | | 600/300 |
| 2003/0208335 A1 * | 11/2003 | Unuma et al. | | 702/141 |
| 2005/0240087 A1 * | 10/2005 | Keenan et al. | | 600/301 |
| 2006/0036183 A1 * | 2/2006 | Sackner et al. | | 600/481 |
| 2006/0195020 A1 * | 8/2006 | Martin et al. | | 600/301 |
| 2007/0293781 A1 * | 12/2007 | Sims et al. | | 600/534 |
| 2010/0063365 A1 * | 3/2010 | Pisani et al. | | 600/301 |
| 2011/0066062 A1 * | 3/2011 | Banet et al. | | 600/534 |

FOREIGN PATENT DOCUMENTS

| | | |
|---|---|---|
| JP | 2001-269332 A | 10/2001 |
| KR | 10-2005-0031538 A | 4/2005 |

* cited by examiner

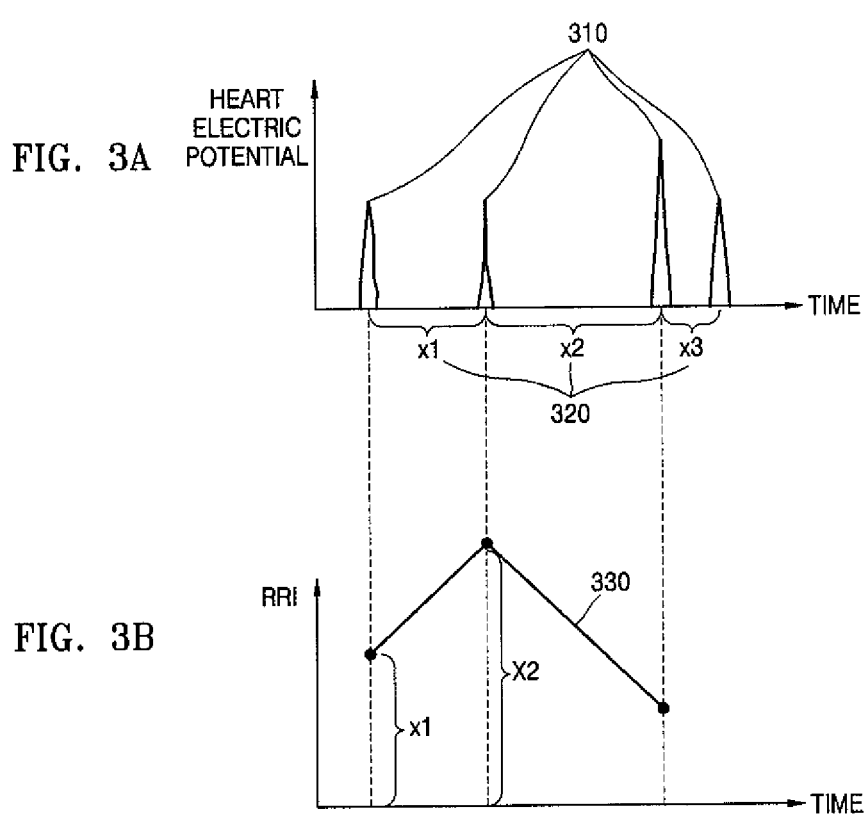

HEALTH CARE APPARATUS AND METHOD

CROSS-REFERENCE TO RELATED PATENT APPLICATIONS

This application claims the benefit of Korean Patent Application No. 10-2005-0064547, filed on Jul. 16, 2005, in the Korean Intellectual Property Office, the disclosure of which is incorporated herein in its entirety by reference.

BACKGROUND OF THE INVENTION

1. Field of the Invention

Apparatuses and methods consistent with the present invention relate to health care, and more particularly, to sensing motions of a health examinee with respect to time, sensing an electric potential signal corresponding to the sensed result from the examinee, and identifying the physical condition of the examinee by analyzing the sensed result.

2. Description of the Related Art

Vital signals that can be sensed from a person such as a health examinee include an electrocardiogram (ECG) signal and an electromyogram (EMG) signal. From the sensed ECG signal, whether or not the heart pulsation of the examinee is being normally generated and the degree of a stress currently felt by the examinee can be determined. Also, from the sensed EMG signal, the amount of calorie consumption by the motion of the examinee can be learned.

Thus, by using the vital signals sensed from the examinee, the physical condition of the examinee can be identified. That is, by using the sensed vital signals, the health index of the examinee can be calculated. At this time, the state of heart pulsation, internal cardial work performed, the balance state of the autonomic nervous system, and the amount of calorie consumption are all examples of health indexes.

Meanwhile, in order to accurately identify the physical condition by using the sensed vital signals, the current motion, i.e., the current motive state, of the examinee should be considered. For example, in an exemplary embodiment, the degree of stress is calculated by using an ECG signal sensed from the examinee when the examinee takes a physical and mental rest. Also, in an exemplary embodiment, the amount of calorie consumption is calculated when the examinee is doing exercise.

The conventional health care apparatuses have a problem that the figures of health indexes cannot be calculated accurately if information on the current motion of the examinee is not given. Also, the conventional apparatuses cannot notify the examinee of the calculated figures of the health indexes in real time.

SUMMARY OF THE INVENTION

The present invention provides a health care apparatus for sensing motions of a health examinee with respect to time, sensing an electric potential signal corresponding to the sensed result from the examinee, and identifying the physical condition of the examinee by analyzing the sensed result.

The present invention also provides a method of sensing motions of a health examinee with respect to time, sensing an electric potential signal corresponding to the sensed result from the examinee, and identifying the physical condition of the examinee by analyzing the sensed result.

The present invention also provides a computer readable recording medium having embodied thereon a computer program for executing a method of sensing motions of a health examinee with respect to time, sensing an electric potential signal corresponding to the sensed result from the examinee, and identifying the physical condition of the examinee by analyzing the sensed result.

According to an aspect of the present invention, there is provided a health care apparatus including: a motion sensing unit sensing the motion of a health examinee with respect to time; a bio-electric potential sensing unit sensing an electric potential signal of the health examinee corresponding to the sensed result; and an analysis unit analyzing the sensed result.

The apparatus may further include a health index calculation unit calculating a desired health index by using the analyzed result, wherein the health index is an index indicating a physical condition of the health examinee.

The motion sensing unit may include a plurality of sensing devices attached to the body of the health examinee.

The plurality of sensing devices may be prepared in an integrated unit or may be prepared at separate places connected through a network.

The bio-electric potential sensing unit may include: a vital signal sensing unit sensing the vital signal of the health examinee in response to the sensed result; and a filtering unit filtering the sensed vital signal in response to the sensed result and outputting the filtered result as the electric potential signal.

The bio-electric potential sensing unit may further include: a matching unit including the sensed result and information on the filtering matching the sensed result, wherein the vital signal sensing unit senses the vital signal indicated in the information matching the sensed result.

The bio-electric potential sensing unit may further include: a matching unit including the sensed result and information on the filtering matching the sensed result, wherein the filtering unit filters the sensed vital signal according to information on the filtering, matching the sensed result.

The electric potential signal may be a vital signal having a frequency band corresponding to the sensed result among vital signals sensible from the health examinee.

The apparatus may further include a user interface unit providing a user interface displaying at least one of the analyzed result and the calculated figure of the health index.

The apparatus may further include a health recognition unit making the health examinee recognize the health condition of the health examinee, by performing a function corresponding to the calculated figure of the health index.

The health condition recognition unit may make the health examinee recognize the health condition of the health examinee, by using at least one of a visual path, a tactile path and an audible path.

The health index may include the state of heart pulsation, internal cardial work performed, the balance state of the autonomic nervous system, or the amount of calorie consumption The vital signal may be an ECG signal or an EMG signal.

The apparatus may further include a storage unit storing the analyzed result and the calculated figure of the health index.

According to another aspect of the present invention, there is provided a health care method including: sensing the motion of a health examinee with respect to time; sensing an electric potential signal of the health examinee corresponding to the sensed result; and analyzing the sensed result.

The method may further include calculating a desired health index by using the analyzed result, wherein the health index is an index indicating a physical condition of the health examinee.

The sensing of the electric potential signal may include: sensing the vital signal of the health examinee in response to the sensed result; and filtering the sensed vital signal according to the sensed result, wherein the filtered result is the electric potential signal.

The method may further include notifying at least one of the analyzed result and the calculated figure of the health index.

The method may further include making the health examinee recognize the calculated figure of the health index, by using at least one of a visual path, a tactile path and an audible path.

The method may further include storing the analyzed result and the calculated figure of the health index.

The health index may include the state of heart pulsation, internal cardial work performed, the balance state of the autonomic nervous system, or the amount of calorie consumption.

The sensing of the motion may be performed by a plurality of sensing devices attached as an integrated unit to the body of the health examinee.

The sensing of the motion may be performed by a plurality of sensing devices that are attached to the body of the health examinee, and prepared at separated places connected through a network.

According to still another aspect of the present invention, there is provided a computer readable recording medium having embodied thereon a computer program for executing a health care method, wherein the method includes: sensing the motion of a health examinee with respect to time; sensing an electric potential signal of the health examinee corresponding to the sensed result; and analyzing the sensed result.

BRIEF DESCRIPTION OF THE DRAWINGS

The above and other aspects the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. However, terms described hereinafter are those defined with consideration of functions in the present invention and can be changed according to a user, the intention of an operator or a convention. Accordingly, definitions should be interpreted based on the contents in the present specification as a whole.

Figure 1:
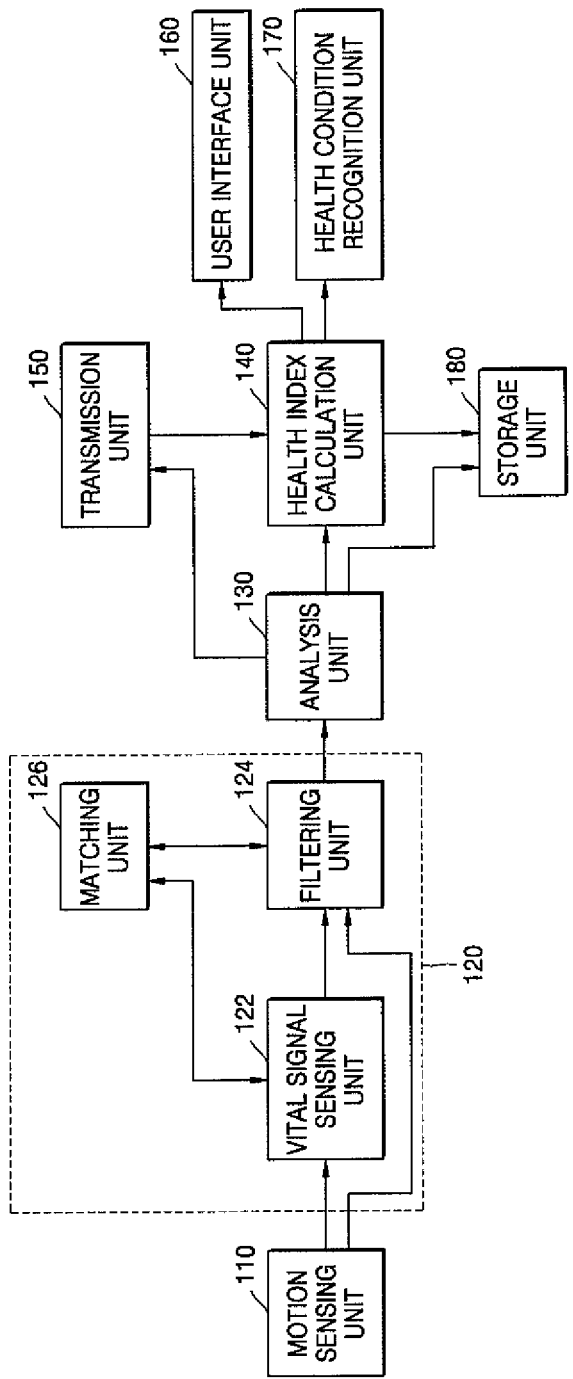
FIG. 1 is a block diagram of an exemplary embodiment of a health care apparatus according to the present invention.

FIG. 1 is a block diagram of an exemplary embodiment of a health care apparatus according to the present invention, and the apparatus may include a motion sensing unit 110, a bio-electric potential sensing unit 120, an analysis unit 130, a health index calculation unit 140, a transmission unit 150, a user interface unit 160, a health condition recognition unit 170, and a storage unit 180. In this exemplary embodiment, the bio-electric potential sensing unit 120 includes a vital signal sensing unit 122, a filtering unit 124, and a matching unit 126.

The motion sensing unit 110 senses the pattern of motions of a health examinee. That is, the motion sensing unit 110 senses the motion of the examinee with respect to time. This motion sensing unit 110 can be constructed with a plurality of sensing devices.

In this case, the plurality of sensing devices can be disposed in an integrated unit. If the plurality of sensing devices are disposed together in a single limited place, it can be said that the plurality of sensing devices are disposed in an integrated unit. For example, if the plurality of sensing devices are disposed together in a patch-shaped place, it can be said that the plurality of sensing devices are disposed in an integrated unit.

Meanwhile, a plurality of sensing devices can be disposed on separate places but connected to each other through a network. That is, each of the plurality of sensing devices can be disposed on different places of the body of the examinee.

In this case, the plurality of sensing devices can be connected to an identical network.

These sensing devices can have at least one of an acceleration sensor function and an angular velocity sensor function. Here, the function of an acceleration sensor is to sense the acceleration of the examinee in an X-axis, Y-axis and Z-axis. Also, the function of an angular velocity sensor is to sense the angular velocity of the examinee. This angular velocity sensor is also referred to as a gyro sensor.

Motions with respect to time sensed by the motion sensing unit 110 include rest, walking, and running. However, rest, walking and running are just examples that can be sensed by the motion sensing unit 110 and other various motions can be sensed by the motion sensing unit 110.

If motions of the examinee are divided into rest, walking and running and sensed by the motion sensing unit 110, the distinguishing criterion of rest, walking, and running for the sensing results should be prepared in advance.

According to the health care apparatus of the present invention, a variety of health indexes can be calculated. Here, the health indexes are arbitrary indexes indicating the physical condition of the examinee. The state of heart pulsation, internal cardial work performed, the balance state of the autonomic nervous system, and the amount of calorie consumption can be examples of health indexes.

Here, by using the state of heart pulsation, whether or not there is a disorder or an abnormality in the pulsation of the heart of the examinee can be determined, and by using the internal cardial work performed, the work of the heart of the examinee when the examinee is doing exercise can be determined. By using the balance state of the autonomic nervous system, the degree of stress felt by the examinee can be determined. Also, by using the amount of calorie consumption, the amount of calories consumed when the examinee is doing exercise can be determined.

Meanwhile, the health indexes, such as the state of heart pulsation, internal cardial work performed, and the balance state of the autonomic nervous system, can be calculated by using an ECG signal sensed from the examinee and the health index such as the amount of calorie consumption can be calculated by using the EMG signal sensed from the examinee.

Here, the ECG signal is a signal indicating the electrical potential generated by a pumping of the heart with respect to time. The EMG signal is a signal indicating the electric potential of muscles with respect to time. These ECG and EMG signals are examples of vital signals that can be sensed from the examinee.

Meanwhile, in order to calculate a health index by using the sensed vital signals, the current motion pattern of the examinee should be considered.

For example, a figure indicating the degree of stress felt by the examinee is calculated in an exemplary embodiment by using an ECG signal sensed from the examinee when the examinee is taking a rest. Accordingly, a figure calculated by using an ECG signal sensed when the examinee is doing exercise can be said to be a less reliable number.

Likewise, when the EMG signal is sensed in order to calculate the amount of calories consumed by the examinee, the motion pattern of the exercise performed by the examinee should be considered. For example, in order to calculate the amount of calories consumed when the examinee rides a bicycle or a skate, in an exemplary embodiment, the amount of calorie consumption is calculated by using an EMG signal sensed in the muscles of the lower part of the body of the examinee. Accordingly, the amount of calorie consumption calculated by using an EMG signal sensed in the muscles of the upper part of the body cannot accurately indicate the amount of calories consumed by the examinee who is exercising the lower part of the body. That is, in order to accurately calculate the amount of calories consumed by the examinee exercising the lower part of the body, an EMG signal sensed in the muscles of the lower part of the body of the examinee should be used.

According to the present invention, a technological structure that senses by itself a current motion pattern of the examinee in a situation where any information on the motion pattern of the examinee is not given, and senses an electric potential signal appropriate to the sensed motion pattern, is implemented by using the bio-electric potential sensing unit 120. Here, the electric signal is a vital signal having a frequency band corresponding to the result sensed by the motion sensing unit 110 among vital signals that can be sensed from the examinee.

The bio-electric potential sensing unit 120 may include the vital signal sensing unit 122 and the filtering unit 124. The bio-electric potential sensing unit 120 senses from the examinee an electric potential signal corresponding to the motion pattern sensed by the motion sensing unit 110.

The vital signal sensing unit 122 senses the vital signal of the examinee in response to the result sensed by the motion sensing unit 110.

At this time, the vital signal sensed in the vital signal sensing unit 122 may be any vital signals that can be sensed in the sensed part of the body. That is, if only the vital signal sensing unit 122 senses any motion pattern irrespective of the contents of the motion pattern sensed in the motion sensing unit 110, all vital signals that can be sensed in the sensed part of the body can be sensed.

Also, the vital signal that is sensed in the vital signal sensing unit 122 may be part of vital signals that can be sensed in the sensed part of the body. That is, the vital signal sensing unit 122 can sense one or more preset vital signals matching the content of the motion pattern sensed in the motion sensing unit 110.

For example, if the examinee taking a rest is sensed by the motion sensing unit 110, in an exemplary embodiment, an ECG signal is sensed from the examinee by the vital signal sensing unit 122. Also, if the examinee exercising the lower part of the body is sensed by the motion sensing unit 110, in an exemplary embodiment, an EMG signal is sensed from the muscles of the lower part of the body of the examinee by the vital signal sensing unit 122.

Also, in response to the result sensed by the motion sensing unit 110, the filtering unit 124 filters the vital signal sensed in the vital signal sensing unit 122 and outputs the filtered result as an electric potential signal.

At this time, if all vital signals that can be sensed in the sensed part of the body are sensed, the filtering unit 124 filters the sensed vital signals in order to generate an electric potential signal having a preset vital signal matching the content of the motion pattern sensed in the motion sensing unit 110. An ECG signal and EMG signal can be examples of the preset vital signals.

For this, the bio-electric potential sensing unit 120 may further include the matching unit 126. At this time, in the matching unit 126, the result sensed in the motion sensing unit 110 is matched with a preset vital signal and information on the preset vital signal is output. Accordingly, the vital signal sensing unit 122 reads information on the preset vital signal matching the result sensed in the motion sensing unit 110, from the matching unit 126 and senses the vital signal indicated by the read information.

Also, the filtering unit 124 can again filter the filtered vital signal in order to generate an electric potential signal having a preset frequency matching the content of the motion pattern sensed in the motion sensing unit 110.

Meanwhile, if part of vital signals that can be sensed in the sensed part of the body are sensed by the vital signal sensing unit 122, the filtering unit 124 can filter the filtered vital signals in order to generate an electric potential signal having a preset frequency matching the content of the motion pattern sensed in the motion sensing unit 110.

For this, the bio-electric potential sensing unit 120 may further include the matching unit 126. At this time, in the matching unit 126 the result sensed in the motion sensing unit 110 is matched with a preset frequency and information on a preset frequency is output. Accordingly, the filtering unit 124 reads information on a frequency matching the result sensed in the motion sensing unit 110, from the matching unit 126 and performs filtering according to the frequency indicated in the read information.

For example, if an ECG signal is sensed in the vital signal sensing unit 122 and the examinee taking a rest is sensed by the motion sensing unit 110, the filtering unit 124 can generate and output an electric potential signal having a frequency from 0.1 Hz to 150 Hz, by passing only an ECG signal having a frequency in the range of 0.1 Hz to 150 Hz and blocking an ECG signal having a frequency in other ranges.

The signal output from the filtering unit 124, that is, the filtered vital signal, is an electric potential signal sensed in the bio-electric potential sensing unit 120.

The analysis unit 130 analyzes the sensed electric potential signal and by using the analyzed result, the health index calculation unit 140 calculates a health index desired to be calculated.

At this time, the analysis unit 130 and the health index calculation unit 140 can be integrated or be connected through a network. That is, the analysis unit 130 and the health index calculation unit 140 can be disposed separately without being disposed in an integrated place.

For example, the analysis unit 130 may be attached to a part of the body of the examinee and the health index calculation unit 140 may be disposed in a computer used by the attending physician. In this case, if the analysis unit 130 and the health index calculation unit 140 are connected through a network, the result analyzed in the analysis unit 130 is transmitted to the health index calculation unit 140.

For this, the transmission unit 150 can be disposed in the health care apparatus according to the present invention. That is, the transmission unit 150 transmits the result analyzed by the analysis unit 130 to the health index calculation unit 140 connected to the analysis unit 130 through a network.

Meanwhile, the user interface unit 160 displays at least one of the result analyzed in the analysis unit 130 and the figure of the health index calculated in the health index calculation unit 140.

The health condition recognition unit 170 notifies the examinee of the figure of the health index calculated in the health index calculation unit 140.

More specifically, the health condition recognition unit 170 compares a preset threshold figure with the figure calculated in the health index calculation unit 140, and with the comparison result, the health condition recognition unit 170 can notify the examinee of the figure.

The threshold figure is a number indicating that a disorder or an abnormality occurs in the physical condition of the examinee, if the calculated figure exceeds the number, or does not reach the number, or corresponds to the number. For example, if the health index calculation unit 140 calculates a health index of a degree of an internal cardial work performed, and if the calculated degree exceeds a threshold, it is necessary for the examinee doing exercise to immediately stop the exercise. In this case, the health condition recognition unit 170 compares the calculated degree of the internal cardial work performed with the threshold, and if the comparison result indicates that the calculated degree exceeds the threshold, the health condition recognition unit 170 notifies the examinee that the exercise should be stopped immediately.

At this time, by using at least one of visual means, tactile means, and audible means, the health condition recognition unit 170 can convey the figure. For this, the health condition recognition unit 170 may include a vibration motor, a speaker, or a display panel, or the like.

For example, when the health condition recognition unit 170 finishing a comparison of the calculated degree of the internal cardial work performed with the threshold, desires to notify the examinee doing exercise that the exercise should be stopped, the health condition recognition unit 170 may vibrate a vibration motor, or sound through a speaker, or display on a display in order to notify the examinee that the exercise should be stopped.

Meanwhile, the storage unit 180 stores at least one of the result analyzed in the analysis unit 130 and the figure of the health index calculated in the health index calculation unit 140.

Figure 2A:
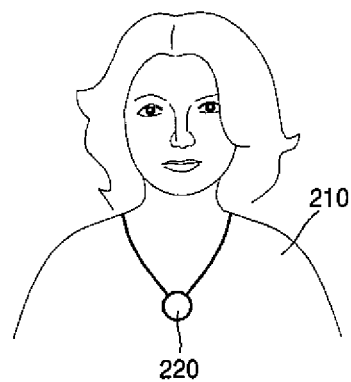
FIGS. 2A and 2B are reference diagrams explaining the health care apparatus according to exemplary embodiments of the present invention shown in FIG. 1.
Figure 2B:
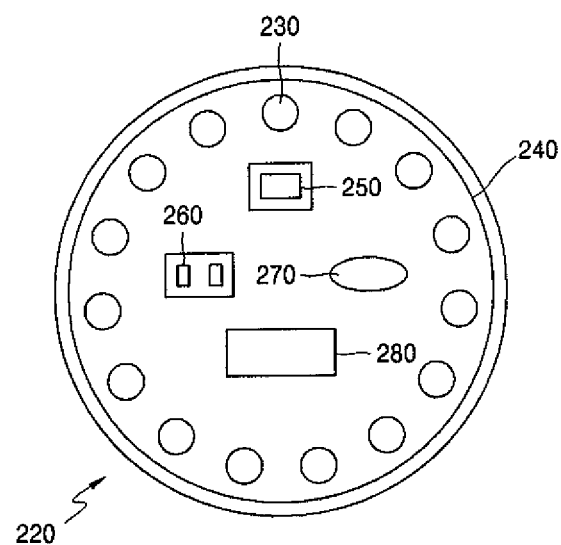

FIGS. 2A and 2B are reference diagrams explaining the health care apparatus according to the present invention shown in FIG. 1.

As shown, the motion sensing unit 110 through the storage unit 180, i.e., the motion sensing unit 110, the bio-electric potential sensing unit 120, the analysis unit 130, the health index calculation unit 140, the transmission unit 150, the user interface unit 160, the health condition recognition unit 170, and the storage unit 180, included in the health care apparatus according to the present invention can be disposed in an integrated unit. In particular, in an exemplary embodiment, the motion sensing unit 110 through the storage unit 180 are disposed in an integrated unit.

FIG. 2A shows an example of implementing the health care apparatus according to the present invention. As shown in FIG. 2A, the motion sensing unit 110 through the storage unit 180 included in the health care apparatus according to the present invention can all be disposed at a same place, i.e., on a device 220. Here, the device 220 may be a circle-shaped device as shown.

Also, the health care apparatus according to the present invention may be disposed in a pendant of a necklace, or unlike the figure, the health care apparatus can be disposed in a medium, for example, a patch, detachably attached to the body of the examinee.

FIG. 2B is a diagram showing details of the health care apparatus 220 shown in FIG. 2A. If the vital signal sensing unit 122 is formed with a plurality of sensing devices, reference number 230 indicates each of the sensing devices.

Meanwhile, reference number 240 indicates the transmission unit 150, reference number 250 indicates the motion sensing unit 110, reference number 260 indicates a photo-plethysmography (PPG) sensor, and reference number 270 indicates a temperature sensor.

That is, the vital signal sensing unit 122 may sense the PPG, or a core temperature. Here, the core temperature is the temperature of a place at a predetermined distance from the skin of a part being examined. The predetermined distance is determined in advance and can be varied.

When the vital signal sensing unit 122 senses the PPG, the health index calculation unit 140 can measure the blood oxygen saturation of the examinee 210. Furthermore, when vital signal sensing unit 122 senses both the PPG and the ECG signal, the health index calculation unit 140 can calculate the blood pressure of the examinee 210.

Also, reference number 280 indicates a control unit and the control unit controls operations of all the units from the vital signal sensing unit 230 through the temperature sensor 270.

Figure 3C:
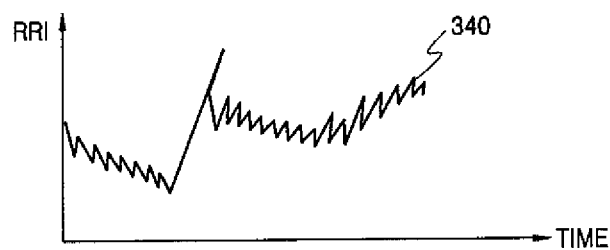
FIGS. 3A, 3B, 3C. 3D and 3E are reference diagrams explaining a process for calculating a stress figure of a health examinee by a health care apparatus according to an exemplary embodiment of the present invention.

FIGS. 3A, 3B, 3C. 3D and 3E are reference diagrams explaining a process for calculating a stress figure of the health examinee 210 by a health care apparatus according to the present invention.

More specifically, FIG. 3A is a timing diagram showing the electric potential of an R-peak value 310 sensed from the examinee 210 with respect to time. In FIG. 3A, x1, x2, and x3 320 indicate R-R intervals (RRI). Here, the RRI is an interval between R-peak values on the time axis.

FIG. 3B is a timing diagram 330 showing RRI values, such as x1, x2, and x3 shown in FIG. 3A, with respect to time. Furthermore, FIGS. 3C and 3D are timing diagrams 340 and 350, respectively, that can be expressed in FIG. 3B and are expressed in a large scale.

Figure 3D:
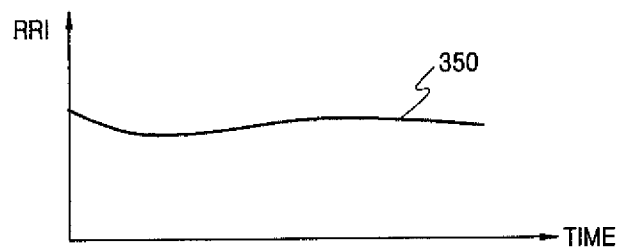

The waveform of the timing diagram 340 shown in FIG. 3C is more random than that of the timing diagram 350 shown in FIG. 3D, and the examinee 210 sensed as the timing diagram 340 shown in FIG. 3C is healthier than the examinee 210 sensed as the timing diagram 350 shown in FIG. 3D.

Figure 3E:
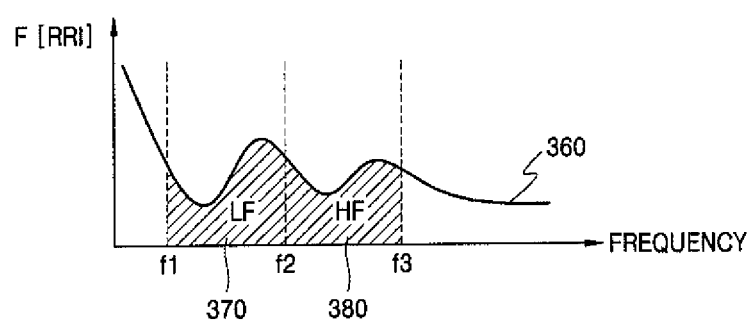

Meanwhile, if the RRI signals in FIGS. 3C and 3D are Fourier transformed, a timing diagram 360 as shown in FIG. 3E can be generated. Here, all of f1, f2 and f3 are preset frequencies and can be varied. For example, f1, f2, and f3 may be 0.04 Hz, 0.1 Hz, and 0.5 Hz, respectively.

Meanwhile, LF shown in FIG. 3E can be expressed as the following equation 1:

$$LF = \int_{f1}^{f2} F[RRI(t)]df \quad (1)$$

Likewise, HF shown in FIG. 3E can be expressed as the following equation 2:

$$HF = \int_{f2}^{f3} F[RRI(t)]df \quad (2)$$

Here, LF is mainly affected by the autonomic nervous system and HF is mainly affected by the para autonomic nervous system. Accordingly, the figure of HF/LF indicates whether or not the mental and body condition of the examinee 210 is in a stable state.

For example, HF/LF=2/3 indicates that the mental and body condition of the examinee 210 is in a stable state. When the health index calculation unit 140 calculates the degree of stress currently felt by the examinee 210, the health index calculation unit 140 calculates an HF/LF figure and 2/3 becomes a threshold figure.

In this case, the health condition recognition unit 170 compares the HF/LF figure calculated by the health index calculation unit 140 with 2/3, and if the result of the comparison indicates that the calculated number exceeds 2/3, the health condition recognition unit 170 can notify the examinee 210 that the examinee 210 is in a tension state, i.e., has an elevated stress level. Meanwhile, if the comparison result indicates that the calculated figure is 2/3 or less than 2/3, the examinee 210 is in a relaxed state and therefore, the health condition recognition unit 170 may not notify the examinee 210.

Figure 4:
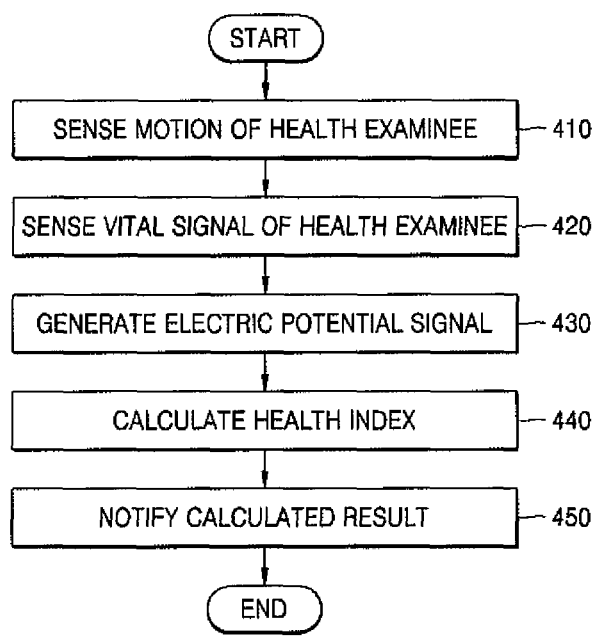
FIG. 4 is a flowchart explaining an exemplary embodiment of a health care method according to the present invention.

FIG. 4 is a flowchart explaining an exemplary embodiment of a health care method according to the present invention. The embodiment is formed with sensing the motion pattern of the examinee 210 and sensing an electric potential signal corresponding to the sensed motion pattern in operations 410, 420 and 430, and calculating a health index by using the sensed electric potential signal and notifying the examinee 210 of the calculated result in operations 440 and 450.

The motion sensing unit 110 senses the motion of the examinee 210 with respect to time in operation 410. The vital signal sensing unit 122 senses a vital signal corresponding to the sensed result from the examinee 210 in operation 420.

Then, the filtering unit 124 filters the vital signal sensed in the vital signal sensing unit 122 according to the sensed result and generates an electric potential signal in operation 430. That is, the electric potential signal is a filtered vital signal.

Accordingly, after the operation 410, the bio-electric potential sensing unit 120 senses an electric signal corresponding to the sensed result from the examinee 210 in the operations 420 and 430.

Then, the analysis unit 130 analyzes the sensed electric potential signal and the health index calculation unit 140 calculates a health index by using the analyzed result in operation 440, and the health condition recognition unit 170 notifies the examinee 210 of the calculated health index in operation 450.

Figure 5:
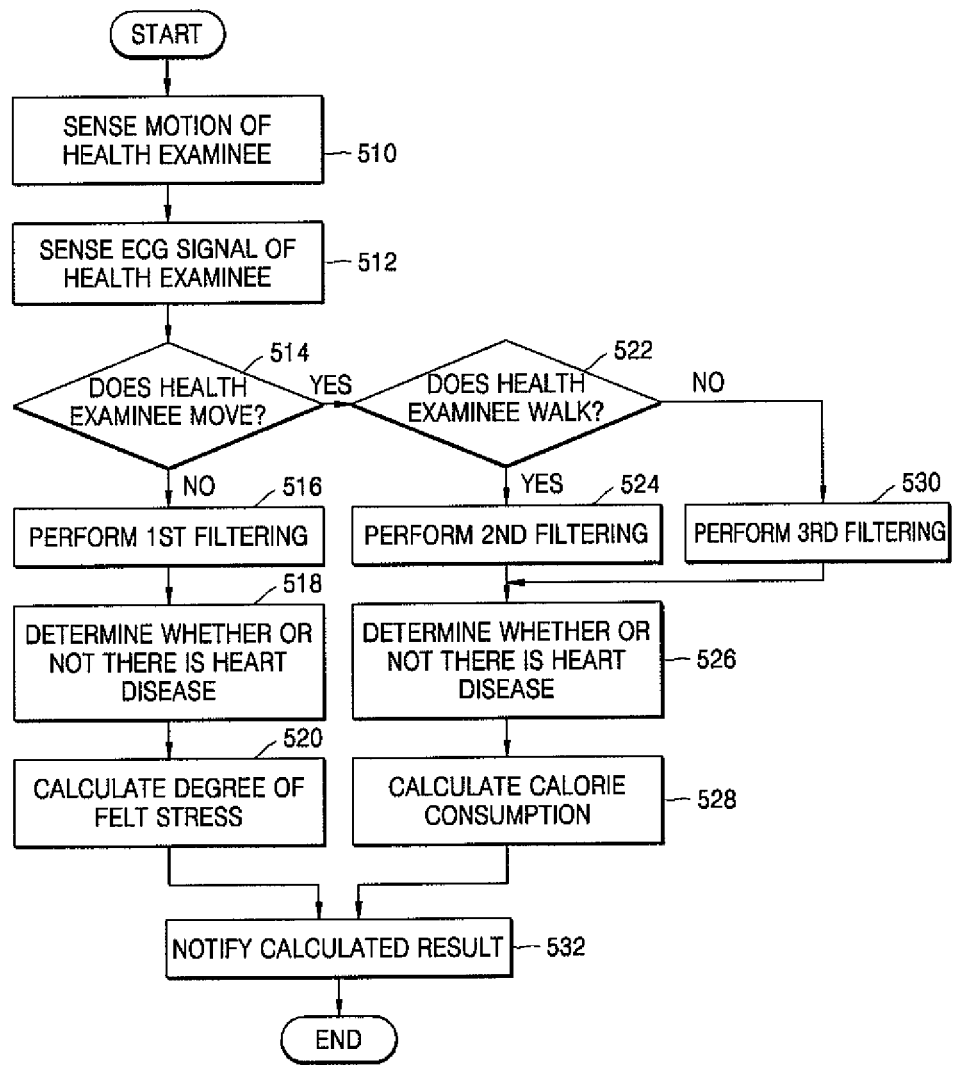
FIG. 5 is a flowchart explaining a principle of managing the state of heart pulsation of a health examinee according to an exemplary embodiment of a health care method of the present invention.

FIG. 5 is a flowchart explaining a principle of managing the state of heart pulsation of a health examinee according to a health care method of the present invention. The flowchart is formed with sensing the motion pattern of the examinee 210 and sensing an electric potential signal corresponding the sensed motion pattern in operations 510, 512, 514 and 516, 522, 524 and 530, and calculating a health index by using the sensed electric potential signal and notifying the examinee 210 of the calculated result in operations 518, 520, 526, 528, and 532.

The motion sensing unit 110 senses the motion of the examinee 210 with respect to time in operation 510. The vital signal sensing unit 212 senses an ECG signal from the examinee 210 in operation 512, and the filtering unit 124 filters the sensed ECG signal according to the result sensed in the motion sensing unit 110.

More specifically, if it is determined in the motion sensing unit 110 that the examinee 210 is taking a rest in operation 514, the filtering unit 124 performs first filtering in operation 516. For convenience of explanation, it is assumed that the first filtering is to pass only frequencies from 0.1 Hz through 150 Hz. In this case, all P, Q, R, S, and T waves of the ECG signal pass the filtering unit 124. Here, the first-filtered vital signal becomes an electric potential signal.

After the operation 516, the analysis unit 130 analyzes the first-filtered vital signal and by using the analyzed result, the health index calculation unit 140 determines whether or not there is a disorder or an abnormality in the pulsation of the heart of the examinee 210 in operation 518. Furthermore, by using the analyzed result, the health index calculation unit 140 calculates the degree of stress felt by the examinee 210 in operation 520.

Meanwhile, if it is determined in the motion sensing unit 110 that the examinee 210 is walking in operation 522, the filtering unit 124 performs second filtering in operation 524. For convenience of explanation, it is assumed that the first filtering is to pass only frequencies from 1 Hz through 60 Hz. In this case, all P, Q, R, S, and T waves of the ECG signal pass the filtering unit 124. Here, the second-filtered vital signal becomes an electric potential signal.

After the operation 524, the analysis unit 130 analyzes the second-filtered vital signal and by using the analyzed result, it is determined whether or not there is a disorder or an abnormality in the pulsation of the heart of the examinee 210 in operation 526. Furthermore, by using the analyzed result, the health index calculation unit 140 calculates the amount of calories consumed by the examinee 210 in operation 528.

Meanwhile, if it is determined in the motion sensing unit 110 that the examinee 210 is running in operation 522, the filtering unit 124 performs third filtering in operation 530. For convenience of explanation, it is assumed that the third filtering is to pass only frequencies from 5 Hz through 30 Hz. In this case, Q, R, and S waves of the ECG signal pass the filtering unit 124. Here, the third-filtered vital signal becomes an electric potential signal.

After the operation 530, the analysis unit 130 analyzes the third-filtered vital signal and by using the analyzed result, the health index calculation unit 140 determines whether or not there is a disorder or an abnormality in the pulsation of the heart of the examinee 210 and in addition, calculates the heart rate of the examinee 210. Furthermore, by using the analyzed result, the health index calculation unit 140 calculates the amount of calories consumed by the examinee 210.

The health condition recognition unit 170 notifies the examinee 210 of the figure calculated in the health index calculation unit 140 in operation 532.

Figure 6:
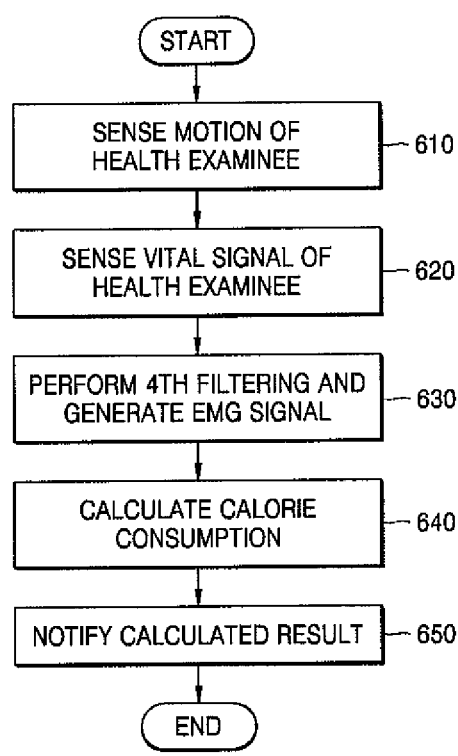
FIG. 6 is a flowchart explaining a principle of calculating the amount of calories consumed by a health examinee according to an exemplary embodiment of a health care method of the present invention.

FIG. 6 is a flowchart explaining a principle of calculating the amount of calories consumed by a health examinee according to a health care method of the present invention. The flowchart is formed with sensing the motion pattern of the examinee 210 and sensing an electric potential signal corresponding the sensed motion pattern in operations 610, 620 and 630, and calculating a health index by using the sensed electric potential signal and notifying the examinee 210 of the calculated result in operations 640 and 650.

The motion sensing unit 110 senses the motion of the examinee 210 with respect to time in operation 610 and the vital signal sensing unit 122 senses all vital signals that can be sensed in the sensed part of the body in operation 620.

Then, the filtering unit 124 filters the vital signal sensed in the vital signal sensing unit 122 according to the sensed result and generates an EMG signal in operation 630. In this case, the EMG signal is an electric potential signal.

Accordingly, after the operation 610 the bio-electric potential sensing unit 120 senses an electric potential signal corresponding to the sensed result from the examinee 210 in operations 620 and 630.

Then, the analysis unit 130 analyzes the sensed EMG signal and by using the analyzed result, the health index calculation unit 140 calculates the amount of calorie consumption in operation 640 in operation 640. The health index recognition unit 170 notifies the examinee 210 of the calculated figure of the amount of the calorie consumption in operation 650.

The present invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion. Also, functional programs, codes, and code segments for accomplishing the present invention can be easily construed by programmers skilled in the art to which the present invention pertains.

While the present invention has been particularly shown and described with reference to exemplary embodiments thereof, it will be understood by those of ordinary skill in the art that various changes in form and details may be made therein without departing from the spirit and scope of the present invention as defined by the following claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

According to the health care apparatus and method of the present invention as described above, by recognizing a current motion of the examinee and sensing an electric potential signal corresponding to the recognized current motion from the examinee, a health index having more reliable figures than those of health index calculated without considering the current motion of the examinee can be calculated.

Meanwhile, according to the health care apparatus and method of the present invention even when information on the current motion of the health examinee is not given, the current motion can be recognized by the apparatus and method such that the health index can be calculated. Furthermore, since the figures of the calculated health index are notified to the health examinee in real time, if the physical condition enters an emergency state, the health examinee can be informed immediately that the physical condition is in an emergency state.

As a result, according to the health care apparatus and method of the present invention, the health examinee can recognize the physical condition in real time and when the physical condition is in an emergency state, the examinee can respond quickly to the emergency situation.

What is claimed is:

1. A health care apparatus comprising:
   a motion sensing unit which senses a motion of a person with respect to time;
   a bio-electric potential sensing unit which senses an electric potential signal of the person corresponding to the sensed motion; and
   an analysis unit, implemented on a processor, which analyzes the sensed electric potential signal to generate an analyzed result,
   wherein the electric potential signal is a vital signal having a frequency band corresponding to the sensed motion among a plurality of vital signals detected from the person,
   wherein the bio-electric potential sensing unit comprises:
   a vital signal sensing unit, implemented on the processor, comprising a plurality of sensing devices, which senses the plurality of vital signals of the person;
   a matching unit, implemented on the processor, which selects the vital signal among the plurality of vital signals based on a result of the sensed motion; selects a frequency band based on the result of the sensed motion; and outputs information on the vital signal and the frequency band; and
   a filtering unit, implemented on the processor, which filters the sensed plurality of vital signals and generates the electric potential signal having the vital signal indicated in the output information among the plurality of vital signals; and further filters the electric potential signal having the vital signal, such that the electric potential has the frequency band that matches the sensed motion indicated in the output information,
   wherein the matching unit selects a sensing device matching a relative body location corresponding to the sensed motion among the plurality of sensing devices, and the selected sensing device senses one or more preset vital signals.

2. The apparatus of claim 1, further comprising a health index calculation unit which calculates a desired health index by using the analyzed result, wherein the health index is an index indicating a physical condition of the person.

3. The apparatus of claim 2, further comprising a user interface unit which displays at least one of the analyzed result and the calculated figure of the health index.

4. The apparatus of claim 2, further comprising a health condition recognition unit which notifies the person of the physical condition of the person.

5. The apparatus of claim 4, wherein the health condition recognition unit notifies the person of the physical condition of the person, by using at least one of visual means, tactile means and audible means.

6. The apparatus of claim 2, wherein the health index comprises state of heart pulsation, internal cardial work performed, balance state of an autonomic nervous system, or amount of calorie consumption.

7. The apparatus of claim 2, further comprising a storage unit which stores the analyzed result and the calculated health index.

8. The apparatus of claim 1, wherein the motion sensing unit comprises a plurality of sensing devices attached to a body of the person.

9. The apparatus of claim 8, wherein the plurality of sensing devices are disposed in an integrated unit or are disposed at separate places connected through a network.

10. The apparatus of claim 1, wherein the vital signal is an electrocardiogram signal or an electromyogram signal.

11. The health care apparatus of claim 1, wherein the sensed motion of the person comprises a movement of a lower part of the person's body and the vital signal is sensed from the lower part of the body corresponding to said movement.

12. The health care apparatus of claim 1, wherein the sensed motion of the person comprises any one of walking and running and the vital signal is sensed at a body limb corresponding to the one of walking and running.

13. A health care method executed by a processor, the method comprising:
   sensing a motion of a person with respect to time;
   sensing an electric potential signal of the person corresponding to the sensed motion; and
   analyzing the sensed electric potential signal to generate an analyzed result,
   wherein the electric potential signal is a vital signal having a frequency band corresponding to the sensed motion among a plurality of vital signals detected from the person,
   wherein the sensing the electric potential signal comprises:
   sensing the plurality of vital signals of the person using one or more sensing device among a plurality of sensing devices;
   selecting the vital signal among the plurality of vital signals based on a result of the sensed motion;
   selecting the frequency band based on the result of the sensed motion; outputting information on the vital signal and the frequency band; and
   filtering the sensed plurality of vital signals and generating the electric potential signal having the vital signal indicated in the output information among the plurality of vital signals; and further filtering the electric potential signal having the vital signal, such that the electric potential has the frequency band that matches the sensed motion indicated in the output information,
   wherein, the sensing the electric potential signal further includes selecting a sensing device matching a relative body location corresponding to the sensed motion among the plurality of sensing devices, and sensing one or more preset vital signals.

14. The method of claim 13, further comprising calculating a desired health index by using the analyzed result, wherein the health index is an index indicating a physical condition of the person.

15. The method of claim 14, further comprising outputting at least one of the analyzed result and the calculated figure of the health index.

16. The method of claim 14, further comprising notifying the person of the calculated health index, by using at least one of visual means, tactile means and audible means.

17. The method of claim 14, further comprising storing the analyzed result and the calculated health index.

18. The method of claim 14, wherein the health index comprises state of heart pulsation, internal cardial work performed, balance state of the autonomic nervous system, or amount of calorie consumption.

19. The method of claim 13, wherein the vital signal is an electrocardiogram signal or an electromyogram signal.

20. The method of claim 13, wherein the sensing the motion is performed by a plurality of sensing devices attached as an integrated unit to a body of the person.

21. The method of claim 13, wherein the sensing the motion is performed by a plurality of sensing devices that are attached to a body of the person, and prepared at separated places connected through a network.

22. The method of claim 13, wherein the sensed motion of the person comprises a movement of a lower part of the person's body and the vital signal is sensed from the lower part of the body corresponding to said movement.

23. The health care apparatus of claim 1, wherein the filtering unit performs a first filtering based on a first condition met by the sensed motion and performs a second filtering based on a second condition met by the sense motion.

24. A non-transitory computer readable recording medium having embodied thereon a computer program for executing a health care method on a processor, wherein the method comprises:
   sensing a motion of a person with respect to time;
   sensing an electric potential signal of the person corresponding to the sensed motion; and
   analyzing the sensed electric potential signal,
   wherein the electric potential signal is a vital signal having a frequency band corresponding to the sensed motion among a plurality of vital signals detected from the person,
   wherein the sensing the electric potential signal comprises:
   sensing the plurality of vital signals of the person using one or more sensing device among a plurality of sensing devices;
   selecting the vital signal among the plurality of vital signals based on a result of the sensed motion;
   selecting the frequency band based on the result of the sensed motion; and
   outputting information on the vital signal and the frequency band; and
   filtering the sensed plurality of vital signals and generating the electric potential signal having the vital signal indicated in the output information among the plurality of vital signals; and further filtering the electric potential signal having the vital signal, such that the electric potential has the frequency band that matches the sensed motion indicated in the output information,
   wherein, the sensing the electric potential signal further includes selecting a sensing device matching a relative body location corresponding to the sensed motion among the plurality of sensing devices, and sensing one or more preset vital signals.

25. The non-transitory computer readable recording medium of claim 24, wherein the sensed motion of the person comprises a movement of a lower part of the person's body and the vital signal is sensed from the lower part of the body corresponding to said movement.

* * * * *